United States Patent

Marrelli et al.

Patent Number: 5,412,326
Date of Patent: May 2, 1995

[54] MEANS AND METHOD FOR ANALYZING A PETROLEUM STREAM

[75] Inventors: John D. Marrelli; Michael G. Durrett; David A. Helms, all of Houston; Lisa L. Pepin, Sugar Land; Gregory J. Hatton, Kingwood, all of Tex.

[73] Assignee: Texaco Inc., White Plains, N.Y.

[21] Appl. No.: 81,714

[22] Filed: Jun. 25, 1993

Related U.S. Application Data

[63] Continuation-in-part of Ser. No. 459,618, Jan. 2, 1990, abandoned.

[51] Int. Cl.$^6$ ............................................. G01N 22/00
[52] U.S. Cl. ..................... 324/640; 324/643; 324/634; 364/577; 364/498
[58] Field of Search ............... 324/640, 639, 643, 642; 364/498, 577

[56] References Cited

U.S. PATENT DOCUMENTS

| | | | |
|---|---|---|---|
| 4,301,400 | 11/1981 | Paap | 324/640 |
| 4,490,676 | 12/1984 | Davis | 324/639 |
| 4,560,002 | 12/1985 | Davis | 324/640 |
| 4,764,718 | 8/1988 | Revus | 324/640 |
| 4,774,680 | 9/1988 | Agar | 73/61.1 R |

Primary Examiner—Kenneth A. Wieder
Assistant Examiner—Jose M. Solis
Attorney, Agent, or Firm—James L. Bailey; Kenneth R. Priem

[57] ABSTRACT

The means and method of the present invention includes a source of microwave energy and associated elements which provide microwave energy to a petroleum stream. Other circuitry include elements which receive microwave energy from the petroleum stream. Electronic apparatus provides at least one outputs utilizing the provided microwave energy, the received microwave energy and known values for 100 percent oil, 100 percent gas and 100 percent water, corresponding to a ratio of gas to liquid. From the readings of attenuation and phase shift, an estimate of the proportions in the mix is extracted by interpolation.

2 Claims, 1 Drawing Sheet

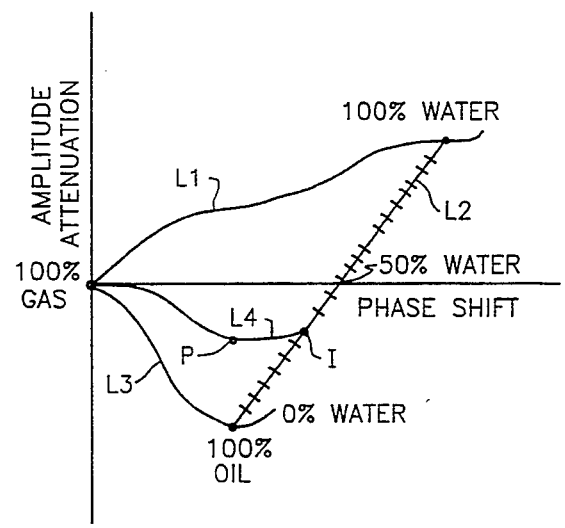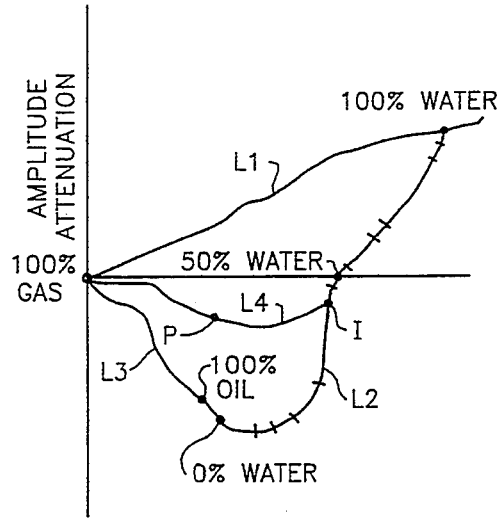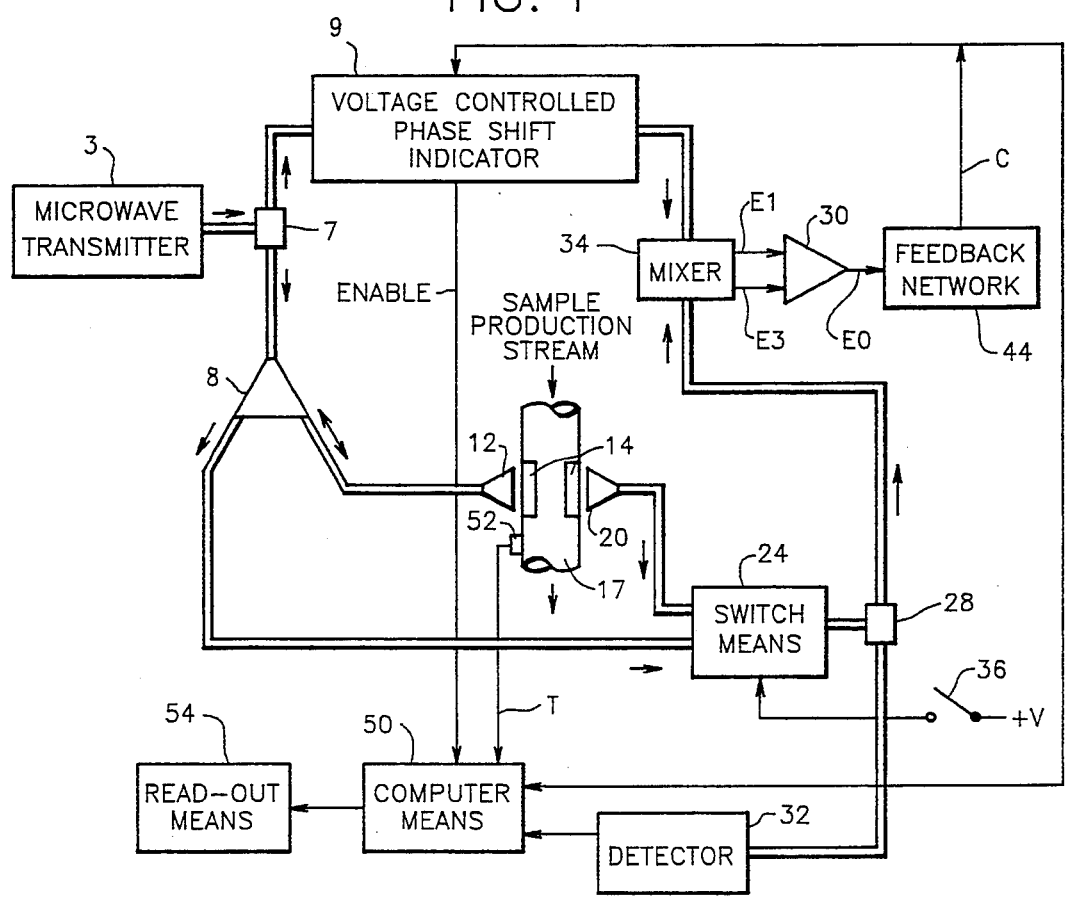

MEANS AND METHOD FOR ANALYZING A PETROLEUM STREAM

CROSS REFERENCE TO RELATED APPLICATIONS

This application is a continuation-in-part of out earlier patent application Ser. No. 07/459,618 filed Jan. 2, 1990, now abandoned, and assigned to the common Assignee.

BACKGROUND OF THE INVENTION

FIELD OF THE INVENTION

The present invention relates to analyzers and analyzing methods in general and, more particularly, to petroleum stream analyzers and analyzing methods.

SUMMARY OF THE INVENTION

The means and method of the present invention includes a source of microwave energy and associated elements which provide microwave energy to a petroleum stream. Other circuitry include elements which receive microwave energy from the petroleum stream. Electronic apparatus provides at least one outputs utilizing the provided microwave energy, the received microwave energy and known values for 100 percent oil, 100 percent gas and 100 percent water, corresponding to a ratio of gas to liquid.

The objects and advantages of the present invention will appear more fully hereinafter from a consideration of the detailed description which follows, taken together with the accompanying drawings wherein one embodiment of the invention is illustrated by way of example. It is to be expressly understood, however, that the drawings are for illustration purposes only and not to be construed as defining the limits of the invention.

DESCRIPTION OF THE DRAWINGS

FIG. 1 is a simplified block diagram of a petroleum stream analyzer constructed in accordance with the present invention.

FIG. 2A is a graphical representation of a map utilized in practicing the present invention for a petroleum stream which is a water-continuous phase.

FIG. 2B is a graphical representation of a map for a petroleum stream which is in an oil-continuous phase.

DESCRIPTION OF THE INVENTION

The present invention is an analyzer which analyzes a produced petroleum stream to determine the water content, the oil content and the gas content of the petroleum stream.

The analyzer shown in FIG. 1 includes a microwave source 3 providing electromagnetic energy, hereinafter referred to as microwave energy. Source 3 is low powered and may use a microwave gun source. Source 3 provides the microwave energies to a directional coupler 7. Directional coupler 7 provides the microwave energy to a circulator 8 and to a conventional type voltage controlled phase shifter 9. All conductance or carrying of microwave energy is accomplished by using conventional type waveguides.

Circulator 8 provides microwave energy to an antenna 12. Antenna 12 provides the microwave energy through a window 14, which may be made of a low dielectric material such as ceramic or Teflon, to a petroleum stream having at least oil and water, passing through a pipe 17. Pipe 17 may be a portion of a pipeline having windows 14 or it may be made of the "window" material. The microwave energy provided by antenna 12 passes through the petroleum stream and another window 14 and is received by an antenna 20. Antenna 20 provides the received microwave energy to a switch means 24 which in turn provides the received microwave as test microwave energy to a directional coupler 28, as hereinafter explained. Directional coupler 28 provides the test microwave energy to a detector 32 and to a mixer 34. Detector 32 provides a signal (E2) corresponding to the intensity of the microwave energy received by antenna 20.

The petroleum stream also reflects some of the microwave energy back to antenna 12 which passes back through antenna 12 to circulator 8. Circulator 8 blocks the reflected microwave energy from feeding back to source 3 and provides the reflected microwave energy to switch means 24. Reflected microwave energy becomes more important as the distance between antennas 12 and 20 increases. This is especially true where a large pipeline carrying the petroleum stream is being monitored.

A positive direct current voltage +V is provided to a switch 36 which is connected to switch means 24. With switch 36 open, switch means 24 provides microwave energy from antenna 20 as test microwave energy. When switch 36 is closed, the reflected microwave energy from circulator 8 is provided by switch means 24 as the test microwave energy.

The microwave energy from voltage controlled phase shifter 9, hereinafter called the reference microwave energy, and the test microwave energy from directional coupler 28, are provided to mixer 34 which mixes them to provide two electrical signals (E3 and E1), representative of the phases of the reference microwave energy and the test microwave energy, respectively.

A differential amplifier 30 provides an output signal EO in accordance with the difference between signals E3 and E1. Signal EO is a function of the phase difference between the reference and is provided to a feedback network 44. Feedback network 44 provides a signal C to voltage control phase shifter 5, controlling the phase of the reference microwave energy, and to a mini-computer means 50. Signal EO, and hence signal C, decreases in amplitude until there is substantially 90° phase difference between the reference microwave energy and the test microwave energy. Voltage control phase shifter 5 indicates the amount of phase shift required to eliminate the phase difference.

Signal (E2) from detector 32 is also provided to computer means 50.

A temperature sensor 52 sensing the temperature of the petroleum stream in pipe 17 and provides a signal T to computer means 50 representative of the sensed temperature.

Phase Shifter 9 also provides an enable signal to computer means 50 allowing computer means 50 to utilize signals T, C and E2. Computer means 50 also provides signal E1 to switch means 4 so that computer means 50 can correlate signal E2 to a particular frequency.

Two maps for the petroleum stream are generated from empirical data as hereinafter explained. One map is for the water-continuous phase of the stream as shown in FIG. 2A, while the second map is for the oil-continuous phase as shown in FIG. 2B.

All of the empirical data is obtained during the calibration of each analysis, in which various mixtures, of known quantities of gas, water and oil, constituents of the mixtures, are provided to pipe 17. The empirical data is stored in the memory of computer means 50.

Five functions, curves or lines may be developed and we may refer to them as a decision curve, which is $f(\emptyset)$; a water cut curve for oil continuous condition as a function $WC_{ocon}(\emptyset)$; a gas correction curve for the oil continuous condition as a function $h(O)$; a water cut curve for the water continuous condition as a function $i(\emptyset)$; and a gas correction curve for the water continuous condition as a function $j(\emptyset)$; where $\emptyset$ is the phase difference, between the test microwave energy and the reference microwave energy. All five functions have the same general form such as for the water cut for the oil continuous condition:

$$WC_{OCON} = X_0 + X_1*(\emptyset) + X_2*(\emptyset^2) + X_3*(\emptyset^3) + X_4*(\emptyset^4), \quad (1)$$

where $X_0$, $X_1$, $X_2$, $X_3$ and $X_4$ are coefficients determined from empirical data. In most cases $X_3$, $X_4$ and greater=0.0.

For one particular mixture having an 24.05 API crude oil, with water having 0.1 $M_{dar}N_uC_l$ salt content at 50°-60° C. for the oil continuous condition, the water cut coefficients from empirical data are: $X_0 = -3.600657E+01$, $X_1 = 8.788994E-01$, $X_2 = 2.155516E-03$. Further, the pure points in amplitude and phase shift are also developed for that mixture which are 100% water: 31.481380952 (amplitude), 433.45714286 (phase shift), and 100% oil: $-0.7708095238$ (amplitude), 40.50952381 (phase shift). Pure gas is taken as zero amplitude ($G_A$), zero phase shift ($G_0$).

In the field, the unknown crude is analyzed and the conclusion is characterized as either oil continuous or water continuous. The data yields a point P which has an amplitude $P_A$ and a phase shift $P_0$. A straight line is generated connecting the pure gas point and point P and it has the general straight line $$L4 = m*P_\emptyset + B, \text{ where } m \text{ is the slope} \quad (2)$$

$$m = (P_A - G_A)/(P_\emptyset - G_0) \quad (3)$$

$$B = m*P_\emptyset - P_A \quad (4)$$

If the emulsion is oil continuous, the intercept Point I having coordinates $I_A$ and $I_O$, on the oil continuous watercut decision curve is determined by setting the straight line function through point P equal to the water cut function for the particular condition (i.e., water continuous or oil continuous) or as $$m*(I_\emptyset) + B = X_\emptyset + X_1*(I_\emptyset) + X_2*(I_\emptyset)^2 \quad (5)$$

which is rewritten as:

$$0.0 = (X_0 - B) + (X_1 - m)*I_\emptyset + X_2*(I_\emptyset)^2 \quad (6)$$

Equation (6) is solved for $I_\emptyset$ using the conventional quadratic equation solution $I_\emptyset = (-b \pm \sqrt{b^2 - 4ac})/2a$ where the c is $(X_0 - B)$, b is $(X_1 - m)$ and a is $X_2$. This solution yields two roots. Only the real roots are accepted. The real root (only one) is the angle of the watercut curve between 100% oil and 100% water (FIG. 2A, 2B) is used.

Assuming that point P requires the use of the map of FIG. 2A, we then solve equation (1) by substituting $I_\emptyset$ for $\emptyset$ to yield watercut.

The gas fraction is a ratio including a first segment of a straight line passing through point P, said first segment being that portion of the straight line between points P and I. The ratio includes a second segment which is that portion of the same straight line between the 100% gas point and point I. The ratio for the gas fraction is the ratio of the first segment to the second segment.

The above methods are repeated using the water continuous map if the emulsion is found to be water continuous.

What is claimed is:

1. A method of analyzing a petroleum stream having oil, water and gas comprising the steps of:
   providing means to inject microwave energy into the petroleum stream;
   providing means to receive microwave energy from the petroleum stream; and
   providing output means utilizing the injected microwave energy, the received microwave energy and known values for 100% oil, 100% gas and 100% water, to relate the known values of 100% oil, 100% gas and 100% water to a phase difference between the injected microwave energy and the received microwave energy, the intensity of the received microwave energy, and a corrected phase shift between the microwave energy being injected and the microwave energy being received to generate two maps utilizing reference points derived from a line L1 connecting the reference points for 100% water and 100% gas, a line L2 connecting the reference points for 100% oil and 100% water, and a line L3 connecting the reference points for 100% oil and 100% gas, one map being for oil continuous mixtures and the other map being for water continuous mixtures;
   determining a measurement point P within the map utilizing the injected microwave energy and the received microwave energy; and
   generating an output in accordance with the relationship of the measurement point p to the map.

2. A method as described in claim 1 further comprising the step of:
   generating a line L4 which passes through the reference point for 100% gas and the measurement point P and intercepts line L2 and point I, and
   developing the ratio of gas to liquid from line L4 comprising a first segment of line L4, from the measurement point P to Point I, to anther segment of line L4 from the reference point for 100% gas to Point I.

* * * * *